(12) United States Patent
Harman

(10) Patent No.: US 8,733,497 B2
(45) Date of Patent: May 27, 2014

(54) FLUID FLOW CONTROLLER

(71) Applicant: Pax Scientific, Inc., San Rafael, CA (US)

(72) Inventor: Jayden David Harman, San Rafael, CA (US)

(73) Assignee: Pax Scientific, Inc., San Rafael, CA (US)

( * ) Notice: Subject to any disclaimer, the term of this patent is extended or adjusted under 35 U.S.C. 154(b) by 0 days.

(21) Appl. No.: 13/778,077

(22) Filed: Feb. 26, 2013

(65) Prior Publication Data

US 2013/0291980 A1 Nov. 7, 2013

Related U.S. Application Data

(63) Continuation of application No. 13/185,490, filed on Jul. 18, 2011, now Pat. No. 8,381,870, which is a continuation of application No. 10/882,412, filed on Jun. 30, 2004, now Pat. No. 7,980,271, which is a continuation of application No. PCT/AU03/00004, filed on Jan. 3, 2003.

(30) Foreign Application Priority Data

Jan. 3, 2002 (AU) ...................................... PR9823

(51) Int. Cl.
*F01N 1/02* (2006.01)
*F01N 1/12* (2006.01)
*F15C 1/16* (2006.01)
*F01N 1/00* (2006.01)
*F01N 1/08* (2006.01)
*F15C 1/00* (2006.01)

(52) U.S. Cl.
USPC ........... 181/249; 181/247; 181/248; 137/808; 138/39

(58) Field of Classification Search
USPC ......... 181/249, 255, 264, 269, 270, 274, 279, 181/280, 281, 247, 248; 137/810, 812, 808; 138/39, DIG. 11
See application file for complete search history.

(56) References Cited

U.S. PATENT DOCUMENTS

| 11,544 A | 8/1854 | Andrews |
| 700,785 A | 5/1902 | Kull |
| 794,926 A | 7/1905 | Crawford |
| 825,010 A | 7/1906 | Snow |

(Continued)

FOREIGN PATENT DOCUMENTS

| AU | 62946/96 | 2/1997 |
| AU | 001388 | 10/2004 |

(Continued)

OTHER PUBLICATIONS

Batchelor, G.K., "An Introduction to Fluid Dynamics", Cambridge Mathematical Library, 2000.

(Continued)

*Primary Examiner* — Edgardo San Martin
(74) *Attorney, Agent, or Firm* — Lewis Roca Rothgerber LLP

(57) ABSTRACT

A fluid pathway is provided with a flow controller in at least a portion of its length wherein the flow controller comprises an active surface capable of influencing the fluid flow through the fluid pathway, the configuration of the active surface conforming to at least one logarithmic curve conforming to the Golden Section.

9 Claims, 12 Drawing Sheets

(56) References Cited

U.S. PATENT DOCUMENTS

| | | |
|---|---|---|
| 871,825 A | 11/1907 | Schupmann |
| 879,583 A | 2/1908 | Pratt |
| 938,101 A | 10/1909 | Winters |
| 943,233 A | 12/1909 | Boyle |
| 965,135 A | 7/1910 | Gibson |
| 969,101 A | 8/1910 | Gibson |
| 1,023,225 A | 4/1912 | Shlosberg |
| 1,272,180 A | 7/1918 | Andresen |
| 1,353,478 A | 9/1920 | Jeffries, Sr. |
| 1,356,676 A | 10/1920 | Well et al. |
| 1,396,583 A | 11/1921 | Krafve |
| 1,471,697 A | 10/1923 | Kubes |
| 1,505,893 A | 8/1924 | Hunter et al. |
| 1,729,018 A | 9/1924 | Siders |
| 1,658,126 A | 2/1928 | Jehle |
| 1,667,186 A | 4/1928 | Bluehdorn |
| 1,709,217 A | 4/1929 | Hamilton |
| 1,713,047 A | 5/1929 | Maxim |
| 1,756,916 A | 4/1930 | Stranahan |
| 1,785,460 A | 12/1930 | Schlotter |
| 1,799,039 A | 3/1931 | Conejos |
| 1,812,413 A | 6/1931 | Reynolds |
| 1,816,245 A | 7/1931 | Wolford |
| 1,872,075 A | 8/1932 | Dolza |
| 1,891,170 A | 12/1932 | Nose |
| 1,919,250 A | 7/1933 | Olson |
| 2,068,686 A | 1/1937 | Lascroux |
| 2,085,796 A | 7/1937 | Fritsch |
| 2,139,736 A | 12/1938 | Durham |
| 2,165,808 A | 7/1939 | Murphy |
| 2,210,031 A | 8/1940 | Greene |
| 2,359,365 A | 10/1944 | Katcher |
| 2,552,615 A | 5/1951 | Baltzer |
| 2,784,797 A | 3/1957 | Bailey |
| 2,879,861 A | 3/1959 | Belsky et al. |
| 2,908,344 A | 10/1959 | Maruo |
| 2,912,063 A | 11/1959 | Barnes |
| 2,958,390 A | 11/1960 | Montague |
| 3,066,755 A | 12/1962 | Diehl |
| 3,071,159 A | 1/1963 | Coraggioso |
| 3,076,480 A | 2/1963 | Vicard |
| 3,081,826 A | 3/1963 | Loiseau |
| 3,082,695 A | 3/1963 | Buschhorn |
| 3,182,748 A | 5/1965 | Wirt |
| 3,215,165 A | 11/1965 | Boadway |
| 3,232,341 A | 2/1966 | Woodworth |
| 3,339,631 A | 9/1967 | McGurty |
| 3,371,472 A | 3/1968 | Krizman, Jr. |
| 3,381,774 A | 5/1968 | Stade |
| 3,407,995 A | 10/1968 | Kinsworthy |
| 3,503,246 A * | 3/1970 | Shiokawa ............... 72/74 |
| 3,584,701 A | 6/1971 | Freeman |
| 3,636,983 A | 1/1972 | Keyser |
| 3,688,868 A | 9/1972 | Gibel et al. |
| 3,692,422 A | 9/1972 | Girardier |
| 3,800,951 A | 4/1974 | Mourlon et al. |
| 3,918,829 A | 11/1975 | Korzec |
| 3,927,731 A | 12/1975 | Lancaster |
| 3,940,060 A | 2/1976 | Viets |
| 3,957,133 A | 5/1976 | Johnson |
| 3,964,841 A | 6/1976 | Strycek |
| 3,970,167 A | 7/1976 | Irvin |
| 4,050,539 A | 9/1977 | Kashiwara et al. |
| 4,182,596 A | 1/1980 | Wellman |
| 4,206,783 A | 6/1980 | Brombach |
| 4,211,183 A | 7/1980 | Hoult |
| 4,225,102 A | 9/1980 | Frosch et al. |
| 4,286,976 A | 9/1981 | Eriksson |
| 4,299,553 A | 11/1981 | Swaroop |
| 4,317,502 A | 3/1982 | Harris et al. |
| 4,323,209 A | 4/1982 | Thompson |
| 4,331,213 A | 5/1982 | Taniguchi |
| 4,505,297 A | 3/1985 | Leech et al. |
| 4,533,015 A | 8/1985 | Kojima |
| 4,540,334 A | 9/1985 | Stahle |
| 4,579,195 A | 4/1986 | Nieri |
| 4,644,135 A | 2/1987 | Daily |
| 4,679,621 A | 7/1987 | Michele |
| 4,685,534 A | 8/1987 | Burstein et al. |
| 4,693,339 A | 9/1987 | Beale et al. |
| 4,699,340 A | 10/1987 | Rethorst |
| 4,823,865 A | 4/1989 | Hughes |
| 4,834,142 A | 5/1989 | Johannessen |
| 4,993,487 A | 2/1991 | Niggemann |
| 4,996,924 A | 3/1991 | McClain |
| 5,010,910 A | 4/1991 | Hickey |
| 5,040,558 A | 8/1991 | Hickey et al. |
| 5,052,442 A | 10/1991 | Johannessen |
| 5,058,837 A | 10/1991 | Wheeler |
| 5,100,242 A | 3/1992 | Latto |
| 5,139,215 A | 8/1992 | Peckham |
| 5,181,537 A | 1/1993 | Powers |
| 5,207,397 A | 5/1993 | Ng et al. |
| 5,220,955 A | 6/1993 | Stokes |
| 5,249,993 A | 10/1993 | Martin |
| 5,261,745 A | 11/1993 | Watkins |
| 5,266,755 A | 11/1993 | Chien |
| 5,312,224 A | 5/1994 | Batchelder et al. |
| 5,320,493 A | 6/1994 | Shih et al. |
| 5,337,789 A | 8/1994 | Cook |
| 5,382,092 A | 1/1995 | Okamoto et al. |
| 5,619,878 A * | 4/1997 | Grosjean et al. ............... 72/56 |
| 5,624,229 A | 4/1997 | Kotzur et al. |
| 5,653,745 A * | 8/1997 | Trescony et al. ............. 623/1.29 |
| 5,661,638 A | 8/1997 | Mira |
| 5,741,118 A | 4/1998 | Shinbara et al. |
| 5,787,974 A | 8/1998 | Pennington |
| 5,824,972 A | 10/1998 | Butler |
| 5,844,178 A | 12/1998 | Lothringen |
| 5,891,148 A | 4/1999 | Deckner |
| 5,934,612 A | 8/1999 | Gerhardt |
| 5,934,877 A * | 8/1999 | Harman ................... 416/223 R |
| 5,943,877 A | 8/1999 | Chen |
| 5,954,124 A | 9/1999 | Moribe et al. |
| 6,050,772 A | 4/2000 | Hatakeyama et al. |
| 6,089,348 A | 7/2000 | Bokor |
| 6,152,258 A | 11/2000 | Deavers et al. |
| 6,179,218 B1 | 1/2001 | Gates |
| 6,241,221 B1 | 6/2001 | Wegner et al. |
| 6,273,679 B1 | 8/2001 | Na |
| 6,374,858 B1 | 4/2002 | Hides et al. |
| 6,382,348 B1 * | 5/2002 | Chen ............................ 181/239 |
| 6,385,967 B1 | 5/2002 | Chen |
| 6,415,888 B2 | 7/2002 | An et al. |
| 6,484,795 B1 | 11/2002 | Kasprzyk |
| 6,588,545 B1 | 7/2003 | Lee |
| 6,604,906 B2 | 8/2003 | Ozeki et al. |
| 6,623,838 B1 | 9/2003 | Nomura et al. |
| 6,632,071 B2 | 10/2003 | Pauly |
| 6,669,142 B2 | 12/2003 | Saiz |
| 6,684,633 B2 | 2/2004 | Jett |
| D487,800 S | 3/2004 | Chen et al. |
| 6,702,552 B1 | 3/2004 | Harman |
| 6,776,194 B2 * | 8/2004 | Houston et al. ................. 138/39 |
| 6,817,419 B2 | 11/2004 | Reid |
| 6,892,988 B2 | 5/2005 | Hugues |
| 6,932,188 B2 | 8/2005 | Ni |
| D509,584 S | 9/2005 | Li et al. |
| 6,959,782 B2 | 11/2005 | Brower et al. |
| 7,073,626 B2 | 7/2006 | Weinhold et al. |
| 7,096,934 B2 | 8/2006 | Harman |
| 7,117,973 B2 | 10/2006 | Graefenstein |
| D539,413 S | 3/2007 | Parker et al. |
| 7,287,580 B2 | 10/2007 | Harman |
| 7,331,422 B2 | 2/2008 | Wall |
| 7,416,385 B2 | 8/2008 | Harman |
| 7,488,151 B2 | 2/2009 | Harman |
| 7,644,804 B2 * | 1/2010 | Harman ....................... 181/279 |
| 7,673,834 B2 | 3/2010 | Harman |
| 7,721,767 B2 * | 5/2010 | Houston et al. ................. 138/39 |
| 7,766,279 B2 | 8/2010 | Harman |
| 7,802,583 B2 * | 9/2010 | Harman ............................ 137/1 |
| 7,814,967 B2 | 10/2010 | Harman |
| 7,832,984 B2 | 11/2010 | Harman |

(56) References Cited

U.S. PATENT DOCUMENTS

| | | | |
|---|---|---|---|
| 7,934,686 B2 * | 5/2011 | Harman | 244/199.1 |
| 7,980,271 B2 * | 7/2011 | Harman | 137/808 |
| 8,328,522 B2 | 12/2012 | Harman | |
| 8,381,870 B2 * | 2/2013 | Harman | 181/249 |
| 8,631,827 B2 | 1/2014 | Harman | |
| 2002/0000720 A1 | 1/2002 | Knowles | |
| 2002/0148777 A1 | 10/2002 | Tuszko et al. | |
| 2003/0012649 A1 | 1/2003 | Sakai et al. | |
| 2003/0190230 A1 | 10/2003 | Ito | |
| 2004/0037986 A1 | 2/2004 | Houston et al. | |
| 2004/0238163 A1 | 12/2004 | Harman | |
| 2004/0244853 A1 | 12/2004 | Harman | |
| 2005/0011700 A1 | 1/2005 | Dadd | |
| 2005/0155916 A1 | 7/2005 | Tuszko et al. | |
| 2005/0205353 A1 | 9/2005 | Chen | |
| 2005/0269458 A1 | 12/2005 | Harman | |
| 2006/0102239 A1 | 5/2006 | Harman | |
| 2006/0249283 A1 | 11/2006 | Harman | |
| 2006/0260869 A1 | 11/2006 | Kim et al. | |
| 2007/0003414 A1 | 1/2007 | Harman | |
| 2007/0025846 A1 | 2/2007 | Harman | |
| 2008/0023188 A1 | 1/2008 | Harman | |
| 2008/0041474 A1 | 2/2008 | Harman | |
| 2008/0145230 A1 | 6/2008 | Harman | |
| 2008/0265101 A1 | 10/2008 | Harman | |
| 2009/0035132 A1 | 2/2009 | Harman | |
| 2009/0308472 A1 * | 12/2009 | Harman | 137/808 |
| 2010/0313982 A1 * | 12/2010 | Harman | 137/808 |
| 2011/0011463 A1 | 1/2011 | Harman | |
| 2011/0129340 A1 | 6/2011 | Harman | |
| 2011/0308884 A1 | 12/2011 | Melcher et al. | |
| 2012/0016461 A1 | 1/2012 | Harman | |

FOREIGN PATENT DOCUMENTS

| | | |
|---|---|---|
| DE | 003315258 | 10/1984 |
| EP | 14257 | 8/1980 |
| EP | 0598253 | 5/1994 |
| FR | 2534981 | 10/1982 |
| FR | 2666031 | 2/1992 |
| GB | 873135 | 7/1961 |
| GB | 2057567 | 4/1981 |
| GB | 2063365 | 5/1981 |
| JP | 98264 | 6/1932 |
| JP | S54129699 | 10/1979 |
| JP | 05332121 | 12/1993 |
| JP | 2000-257610 | 9/2000 |
| JP | D1243052 | 2/2005 |
| SU | 431850 | 6/1974 |
| SU | 738566 | 6/1980 |
| SU | 850104 | 7/1981 |
| SU | 858896 | 8/1981 |
| SU | 1030631 | 7/1983 |
| TW | 565374 | 3/2002 |
| TW | M287387 | 2/2006 |
| WO | WO 81/03201 | 11/1981 |
| WO | WO 87/07048 | 11/1987 |
| WO | WO 89/08750 | 9/1989 |
| WO | WO 9703291 | 1/1997 |
| WO | WO 00/38591 | 7/2000 |
| WO | WO 01 14782 | 3/2001 |
| WO | WO 03056139 | 7/2003 |
| WO | WO 03056190 | 7/2003 |
| WO | WO 03056228 | 7/2003 |
| WO | WO 03056269 | 7/2003 |
| WO | WO 2005/003616 | 1/2005 |
| WO | WO 2005/045258 | 5/2005 |
| WO | WO 2005/073561 | 8/2005 |
| WO | WO 2008/042251 | 4/2008 |

OTHER PUBLICATIONS

Derwent Abstract Accession No. 51960 E/25, SU 858896 A (Onatskii P A), (Aug. 1981).
Derwent Abstract Accession No. E6575C/21, SU 687306A (Leningrad Forestry Acord) Sep. 28, 1977.
Derwent Abstract Accession No. K2273W/37, SU431850 A (Fishing Ind Exp), (Apr. 1975).
Derwent Abstract Accession No. L0015B/47, SE 7803739 A (Ingenjorsfirma Garl) Nov. 5, 1979.
Derwent Abstract Accession No. N8420 E/42, SU 887876 A (AS Ukr Hydromechani) Dec. 7, 1981.
Derwent Abstract Accession No. 85-073498/12, SU 1110986 A (Korolev A S) Aug. 3, 1984.
Derwent Abstract Accession No. 87-318963/45, Class Q56, SU 1291726 A (Makeevka Eng Cons) Feb. 23, 1987.
Derwent Abstract Accession No. 89-075095/10, SU 1418540 A (As Ukr Hydrodynamic) Aug. 23, 1988.
Derwent Abstraction Accession No. 89-157673, SU 1437579 A (Lengd Kalinin Poly) Nov. 15, 1988.
Derwent Abstract Accession No. 91-005279, SU 1560887 A (Sredaztekhenergo En) Apr. 30, 1990.
Derwent Abstract Accession No. 93-375668/47, SU 1756724 A (Odess Poly) Aug. 30, 1992.
Derwent Abstract Accession No. 97-198067/18, JP 09053787 A (Kajima Corp) Feb. 25, 1997.
Derwent Abstract Accession No. 97-546288/50, JP 09264462 A (Sekisui Chem Ind Co. Ltd.) Oct. 7, 1997.
Derwent Abstract Accession No. 99-249047/32, Class Q51, Q57, Q75, Q78, JP 11072104 A (Saito Jidosha Shatai Kogyo KK) Mar. 16, 1999.
Derwent Abstract Accession No. 1999-380417/32, JP 11148591 A (TLV Co. Ltd.) Jun. 2, 1999.
Dismuke's Message Board; http:wwwradiodismuke.com/forum/index.php?showtopic=threaded$pid=.
Foster et al., K., Fluicidics Components and Circuits, Wiley-Interscience, London, 1971, pp. 219-221.
Karassik et al., "Pump Handbook," 1976, McGraw-Hill, Inc, pp. 2-12 and 2-13.
Knott, Dr. Ron, "The Golden Section Ratio: Phi," Available at http://www.mcs.surrey.ac.uk/Personal/R.Knott/Fibonacci/phi.html (last accessed Mar. 17, 2006).
McLarty, W., et al., "Phi Geometry: Impeller & Propeller Design for Fluids Handling," Oct. 1999, Offshore Magazine, p. 123 (and continued).
Merriam-Webster Online Dictionary, 2010 http://www.merriam-webster.com/dictionary/spiral, Feb. 23, 2010, two pages.
Merriam-Webster Online Dictionary, 2010 http://www.merriam-webster.com/dictionary/curve, Feb. 23, 2010, two pages.
Merriam-Webster Online Dictionary, 2010 http://www.merriam-webster.com/dictionary/vortex, Feb. 23, 2010, two pages.
Merriam-Webster Online Dictionary, 2010 http://www.merriam-webster.com/dictionary/vortical, Feb. 23, 2010, two pages.
Schoonmaker, Stephen J.,The CAD Guidebook, A Basic Manual for Understanding and Improving Computer-Aided Design, Marcel Dekker, Inc., New York, 2002.
www.taillightking.com/images/Hood-FenderOrnaments/Hood_Ornaments Pics/.
Patent Abstracts of Japan, Publication No. 2000-168632, Jun. 20, 2000, "Low Air Resistance Vehicle Body Using Vortex Ring.".
PCT Application No. PCT/US07/20916, Search Report and Written Opinion mailed Sep. 4, 2008.
Taiwan Application No. 096136653, Office Action dated Nov. 21, 2011.
U.S. Appl. No. 10/882,412, Final Office Action mailed Jul. 22, 2010.
U.S. Appl. No. 10/882,412, Office Action mailed Feb. 18, 2010.
U.S. Appl. No. 10/882,412, Office Action mailed May 21, 2009.
U.S. Appl. No. 10/882,412, Final Office Action mailed Jun. 6, 2006.
U.S. Appl. No. 10/882,412, Office Action mailed Nov. 25, 2005.
U.S. Appl. No. 10/882,412, Final Office Action mailed Jul. 12, 2005.
U.S. Appl. No. 10/882,412, Office Action mailed Jan. 28, 2005.
U.S. Appl. No. 10/882,412, Office Action mailed Dec. 14, 2004.
U.S. Appl. No. 11/323,137, Office Action mailed Oct. 27, 2009.
U.S. Appl. No. 11/323,137, Final Office Action mailed Jul. 7, 2009.
U.S. Appl. No. 11/323,137, Office Action mailed Jan. 27, 2009.
U.S. Appl. No. 11/323,137, Office Action mailed Dec. 3, 2007.
U.S. Appl. No. 11/323,137, Final Office Action mailed Mar. 27, 2007.

(56) References Cited

OTHER PUBLICATIONS

U.S. Appl. No. 11/323,137, Office Action mailed Oct. 13, 2006.
U.S. Appl. No. 11/323,137, Office Action mailed Mar. 16, 2006.
U.S. Appl. No. 11/906,060, Office Action mailed Jul. 12, 2011.
U.S. Appl. No. 11/924,144, Office Action mailed Feb. 23, 2009.
U.S. Appl. No. 12/484,998, Final Office Action mailed Jun. 20, 2012.
U.S. Appl. No. 12/484,998, Office Action mailed Jan. 12, 2012.
U.S. Appl. No. 12/862,637, Office Action mailed Apr. 11, 2013.
U.S. Appl. No. 12/862,637, Final Office Action mailed Jun. 14, 2011.
U.S. Appl. No. 12/862,637, Office Action mailed Feb. 7, 2011.
U.S. Appl. No. 13/185,490, Office Action mailed Jun. 15, 2012.
U.S. Appl. No. 14/103,593, Jayden D. Harman, Fluid Flow Control Device, Dec. 11, 2013.

\* cited by examiner

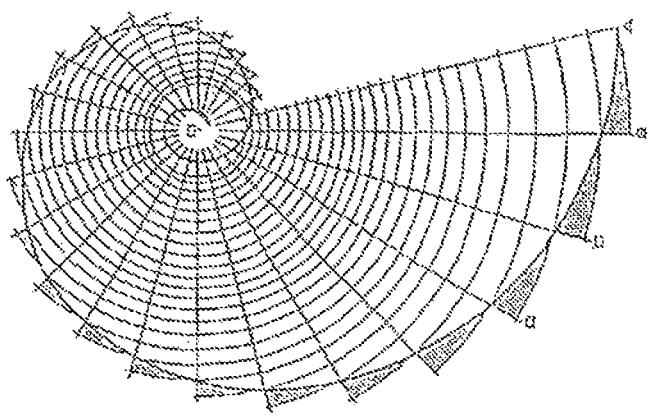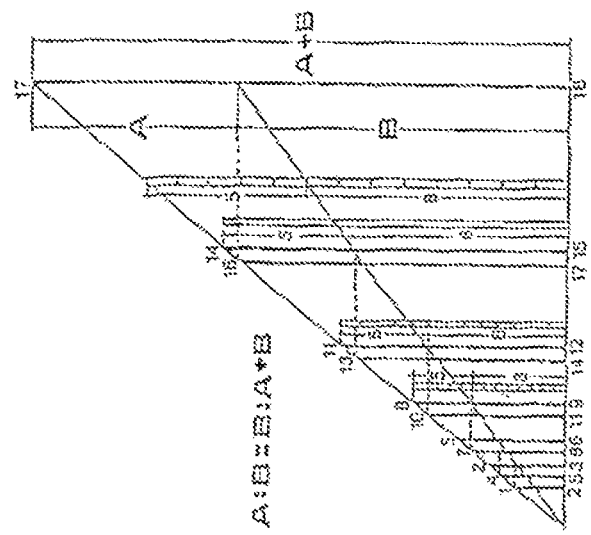
Fig. 1
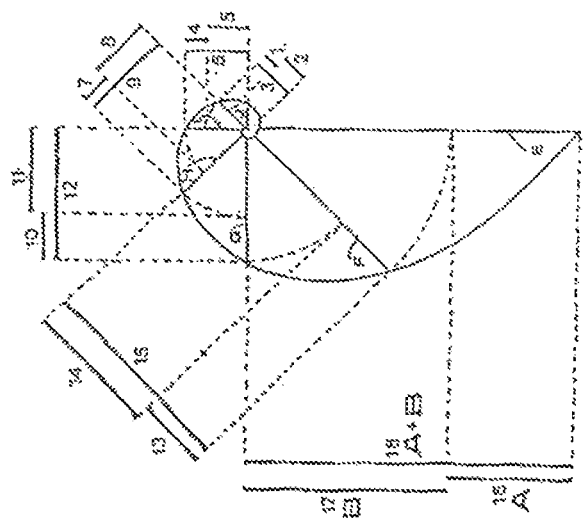

FLUID FLOW CONTROLLER

CROSS REFERENCES TO RELATED APPLICATIONS

This application is a continuation and claims the priority benefit of U.S. patent application Ser. No. 13/185,490 filed Jul. 18, 2011 now U.S. Pat. No. 8,381,870 and entitled "Fluid Flow Controller", which is a continuation and claims the priority benefit of U.S. patent application Ser. No. 10/882,412 filed Jun. 30, 2004 now U.S. Pat. No. 7,980,271, which is a continuation and claims the priority benefit of Patent Cooperation Treaty application number PCT/AU03/00004 filed Jan. 3, 2003, which in turn claims the priority benefit of Australian patent application number PR 9823 filed Jan. 3, 2002. The disclosure of the aforementioned applications is incorporated herein by reference.

The present application is related to U.S. patent application Ser. No. 11/323,137 filed Dec. 29, 2005 and entitled "Fluid Flow Control Device."

FIELD OF THE INVENTION

The present invention relates to ducts adapted to convey a fluid. Examples of the particular applications of the invention include plumbing systems, air-conditioning ducts, cardiovascular stents, dust precipitators, sound attenuators, mufflers and chambers, exhaust pipes, or ducts where optimized adiabatic expansion or contraction is desired.

BACKGROUND ART

Generally, devices which direct, influence, or carry fluid flow utilise a duct which has length but is round in cross section, such as water pipe; or flat sided in cross section such as many air conditioning systems. The principal difficulty with previous arrangements however, has been turbulence created within the fluid flow which reduces efficiency.

In extreme circumstances, in the case of liquids, the turbulence can result in cavitation, which not only reduces the operational efficiency of the duct but can result in inefficiencies, noise, heating, sedimentation of suspended solids, accelerated electrolysis or corrosion through oxygenation of the fluid, and destructive influences upon the structure of the duct. In cardiovascular devices such as straight-sided stents, deleterious cavitation and/or plaque deposits can occur. In adiabatic expansion devices such as steam or jet turbines, the rate of adiabatic expansion or contraction can be retarded by non optimization of the chamber geometry. This can result in significant inefficiencies.

It is an object of this invention to provide a duct which can facilitate fluid flow by reducing the degree of extraneous turbulence to which the fluid is subjected in its passage through the duct. This object is attained by providing a duct which is intended to induce fluid flow into a pattern of movement wherein the resistance to the fluid flow and turbulence to which the fluid flow is subjected are reduced.

In order to effect this object, the surfaces and/or shape of the duct are intended to provide a fluid pathway which conforms generally to the curve of a logarithmic configuration substantially or in greater part conforming to the Golden Section geometric ratio.

All fluids when moving under the forces of nature tend to move in spirals or vortices. These spirals or vortices generally comply with a three-dimensional mathematical logarithmic progression known as the Golden Section or a Fibonacci-like Progression. The invention enables fluids to move over the surfaces of the duct in their naturally preferred way in centripetal vortical rotation, thereby reducing inefficiencies created through turbulence and friction which are normally found in apparatus commonly used for carrying fluid flow.

It may be seen that the more closely a fluid pathway is configured to conform to the Golden Section, the more efficient the duct becomes. However any significant compliance, in part, to the Golden Section will result in improvement over state of the art ducts.

SUMMARY OF THE INVENTION

In a first claimed embodiment of the present invention, a duct disclosed that may be configured to facilitate a change of direction in the flow of a fluid. The duct includes an inlet and an outlet for receiving and expelling fluid, respectively. The inlet corresponds to a first direction of fluid flow whereas the outlet concerns a second direction that differs from the direction of the inlet. An intermediate pathway is situated between the inlet and outlet. The pathway excludes a substantially right angle bend but includes a curvature that induces a vortical flow that reduces turbulence in fluid flow as a fluid traverses the pathway.

In a second claimed embodiment, a duct is provided and that may be configured to facilitate flow of a fluid. The duct includes an inlet, outlet and intermediate pathway. A portion of the intermediate fluid pathway includes a spiral twist that induces a spiral flow that reduces turbulence as the fluid traverse the intermediate pathway.

A further claimed embodiment of the present invention is for a cardiovascular stent that reduces fatty deposits when disposed in a blood flow pathway. The stent includes an inlet, outlet, and intermediate fluid pathway. A portion of the intermediate fluid pathway includes a helical twist that induces a spiral flow that, in turn, reduces turbulence thereby inhibiting the formation of fatty deposits as blood traverses the blood flow pathway.

A fourth claimed embodiment of the present invention is for a fluid flow controller that reduces turbulence in fluid flow. The controller includes an inlet for receiving the fluid, an outlet for expelling the fluid, and an intermediate fluid pathway between the inlet and the outlet. The intermediate fluid pathway conforms substantially to the form of a shell configuration from the phylum Mollusca, class Gastropoda, genus *Volutidae*. The shell configuration of the intermediate fluid pathway induces a spiral flow that reduces turbulence in the fluid flow.

A final claimed embodiment of the present invention provides for a system for attenuating sound in a combustion engine. The system includes a combustion engine that emits a gas flow resulting from a combustible reaction. An exhaust pipe is coupled to and extends away from the combustion engine, which servers to channel the gas flow away from the combustion engine. The system further includes an attenuation chamber coupled to the exhaust pipe by an inlet, which is configured to receive the gas flow channeled away from the combustion engine by the exhaust pipe. The attenuation chamber is larger in volume than the inlet thereby allowing the gas flow to expand within the attenuation chamber. The expansion of the gas flow results in a decrease in the speed of the gas flow as the gas flow passes through an outlet coupled to the attenuation chamber. The decrease in speed of the gas flow results in a reduction in audible sound associated with the gas flow.

BRIEF DESCRIPTION OF THE DRAWINGS

The description is made with reference to the accompanying drawings, of which:

FIG. 1 illustrates the form of the Golden Section;

DETAILED DESCRIPTION

Figure 2:
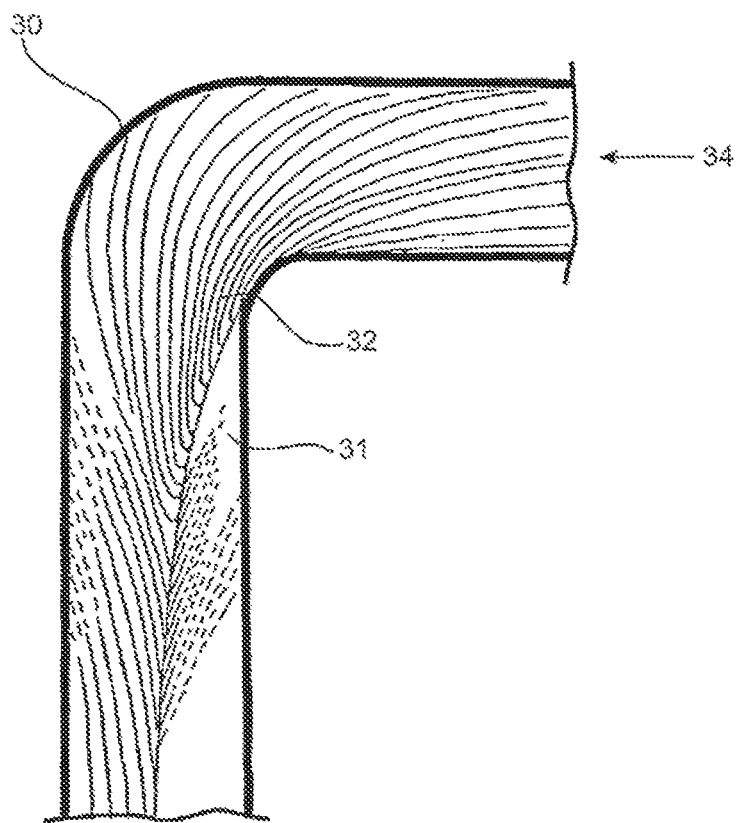
FIG. 2 is a sectional view of conventional ducting at a right angle bend illustrating the nature of the fluid flow created at the bend.

Each of the embodiments is directed to a duct which provides a fluid pathway which can be utilised to convey a fluid.

As stated previously, it has been found that all fluids when moving under the influence of the natural forces of Nature tend to move in spirals or vortices. These spirals or vortices generally comply with a mathematical progression known as the Golden Ratio or a Fibonacci like Progression.

Each of the embodiments serves to, in the greater part, enable fluids to move in their naturally preferred way, thereby reducing inefficiencies created through turbulence and friction which are normally found in apparatus commonly used for propagating fluid flow. Previously developed technologies have generally been less compliant with natural fluid flow tendencies.

The greater percentage of the surfaces of the ducts of each of the embodiments described herein are generally designed in the greater part, in accordance with the Golden Section or Ratio and therefore it is a characteristic of each of the embodiments that the duct provides a fluid pathway which is of a spiralling configuration and which conforms at least in greater part to the characteristics of the Golden Section or Ratio. The characteristics of the Golden Section are illustrated in FIG. 1 which illustrates the unfolding of the spiral curve according to the Golden Section or Ratio. As the spiral unfolds the order of growth of the radius of the curve which is measured at equiangular radii (eg E, F, G, H, I and J) is constant. This can be illustrated from the triangular representation of each radius between each sequence which corresponds to the formula of a:b=b:a+b which conforms to the ratio of 1:0.618 approximately and which is consistent through out the curve.

It is a characteristic of each of the embodiments that the curvature of the surfaces which form the duct takes a two dimensional or three dimensional shape equivalent to the lines of vorticity or streak lines found in a naturally occurring vortex, and which substantially or in the greater part conform to the characteristics of the Golden Section or Ratio and that any variation in cross-sectional area of the fluid pathway also substantially or in greater part conforms to the characteristics of the Golden Section or Ratio. Furthermore it has been found that the characteristics of the Golden Section or Ratio are found in nature in the form of the external and internal configurations of shells of the phylum Mollusca, classes Gastropoda and Cephalopoda and it is a common characteristic of at least some of the embodiments that the fluid pathway defined by the duct corresponds generally to the external or internal configuration of shells of one or more of the genera, of the phylum Mollusca, classes Gastropoda and Cephalopoda.

It has been found that it is a characteristic of fluid flow that, when it is caused to undergo a fluid flow through a pathway having a curvature substantially or in greater part conforming to that of the Golden Section or Ratio that the fluid flow over the surfaces is substantially non-turbulent and as a result has a decreased tendency to cavitate. As a result, fluid flow over the surface is more efficient than has been encountered in previous instances where the pathway does not substantially or in greater part correspond to that of the Golden Section. As a result of the reduced degree of turbulence which is induced in the fluid in its passageway through such a pathway, the ducts according to the various embodiments can be used for conducting fluid with less noise, wear and with a greater efficiency than has previously been possible with conventional ducts of equivalent dimensional characteristics.

Figure 3:
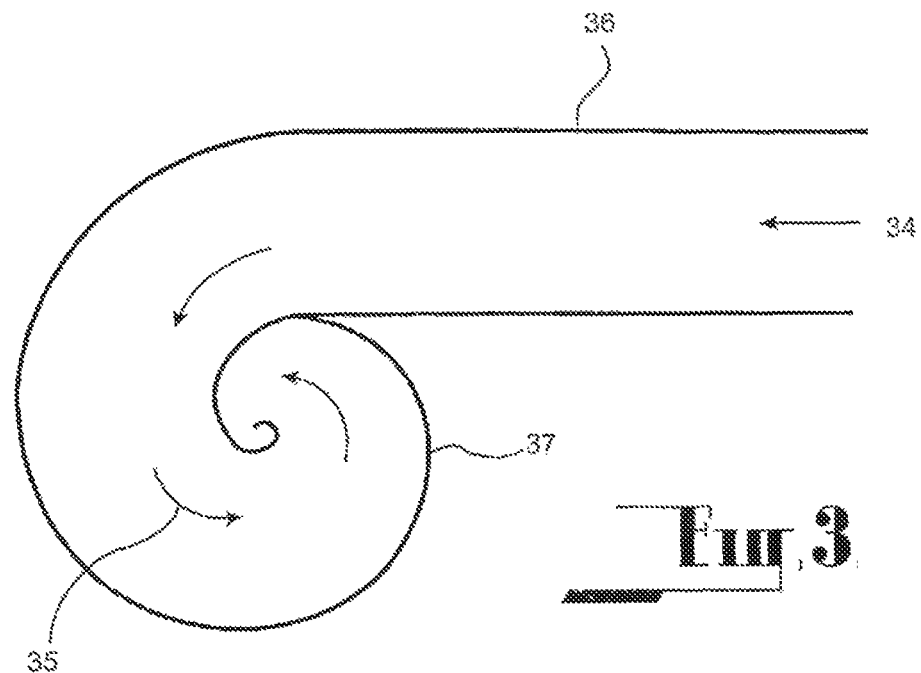
FIG. 3 is an elevation of a duct according to a first embodiment incorporating a right-angular change in direction.
Figure 4:
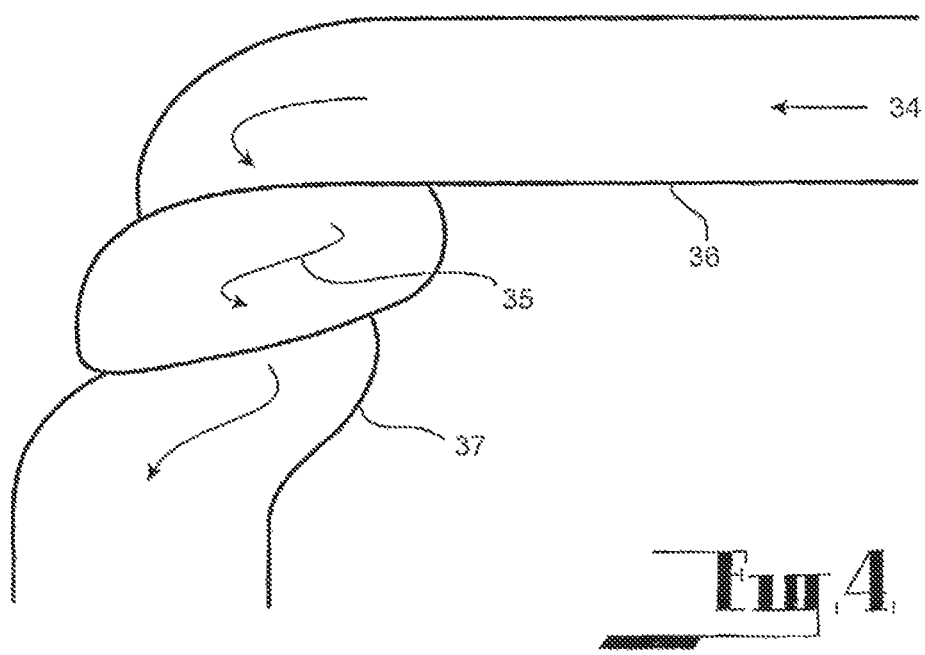
FIG. 4 is a side elevation of a duct according to the first embodiment.

A first embodiment shown in FIG. 3 and FIG. 4 relates to a duct section which facilitates the change in direction of fluid or fluid pathways within plumbing or ducting systems such as water pipes or air conditioning systems.

As can be seen in FIG. 2, a conventional right angle bend (30) in pipe or ducting results in fluid flow that is less than optimal. Streamlines show a low-pressure area (31) and a high-pressure area (32). This can result in turbulence, cavitation, sedimentation and corrosion as well as increasing energy losses in the fluid movement (34). This can result in increased pumping costs and reduced pressure at the outlet.

This form of the embodiment shown in FIGS. 3 and 4 provides a duct (36) specifically designed to induce the fluid (34) to move in accordance with the laws of Nature whilst changing its direction. As mentioned previously, the duct is designed having a pathway having a curvature (37) substantially or in greater part conforming to that of the Golden Section or Ratio. The fluid is thereby induced into vortical flow (35) the greater part of which conforms to the Golden Section or Ratio.

While the first embodiment illustrates the considerable advantages to be gained from a duct designed in accordance with the principles discussed above where there is a discontinuity in the flow of the fluid being conveyed, advantages are available even where the flow is substantially linear.

Figure 5:
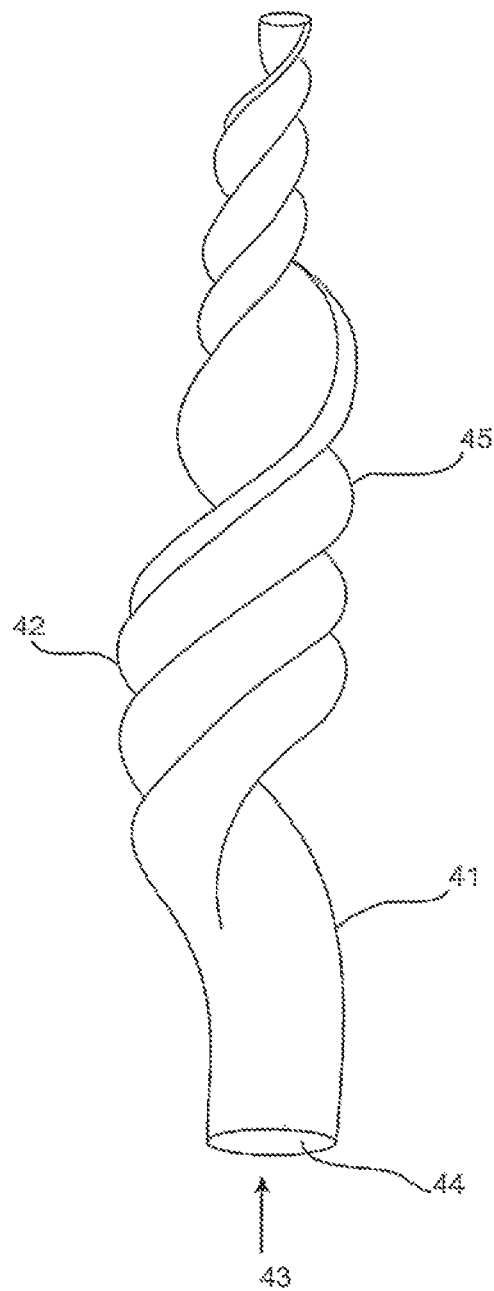
FIGS. 5 is an isometric views of a duct according to a second embodiment.
Figure 6:
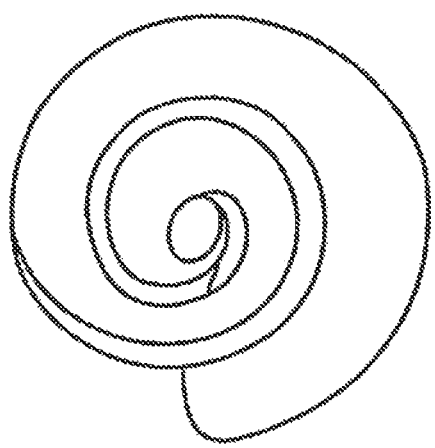
FIGS. 6 is an end view of a duct according to the second embodiment.

A second embodiment shown in FIGS. 5 and 6 relates to a duct (41) providing a twisting pathway (42) for fluids where the pathway conforms to the Golden Section or Ratio. As fluid (43) flows through the inside (44) of the duct, it is urged to conform to natural flow spiral characteristics, which minimize extraneous turbulence.

In an adaptation of the second embodiment, there is provided a flow controller having the form as shown in FIG. 5 and 6, the flow controller adapted to be located within a fluid pathway. In this form the flow of the fluid is around the outside of the flow controller. It is therefore the external surface of the flow controller which is active and is designed to conform to the Golden Section. However, in this adaptation, the flow controller may be hollow which allows the fluid to flow through it internally.

Figure 7:
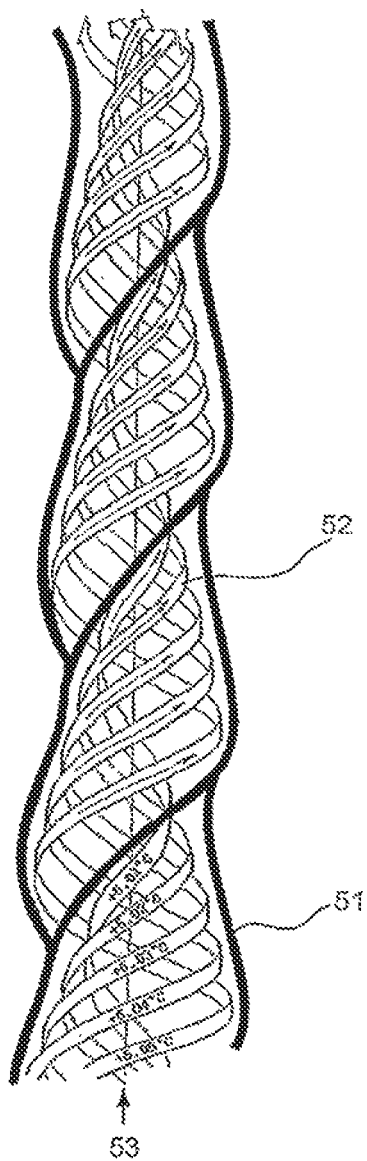
FIG. 7 is an diagrammatic view of a duct or stent according to a third embodiment.
Figure 8:
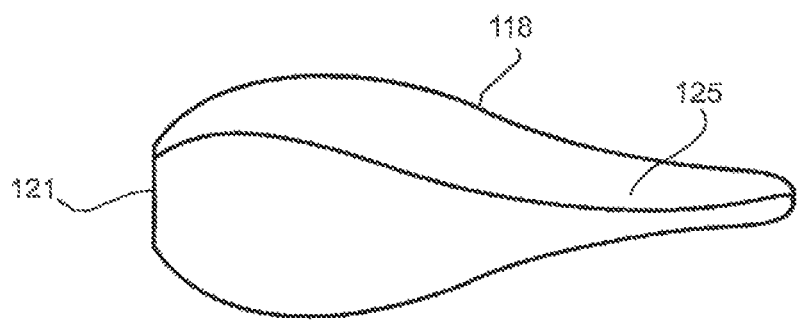
FIG. 8 is a side elevation of a duct according to a fourth embodiment.
Figure 9:
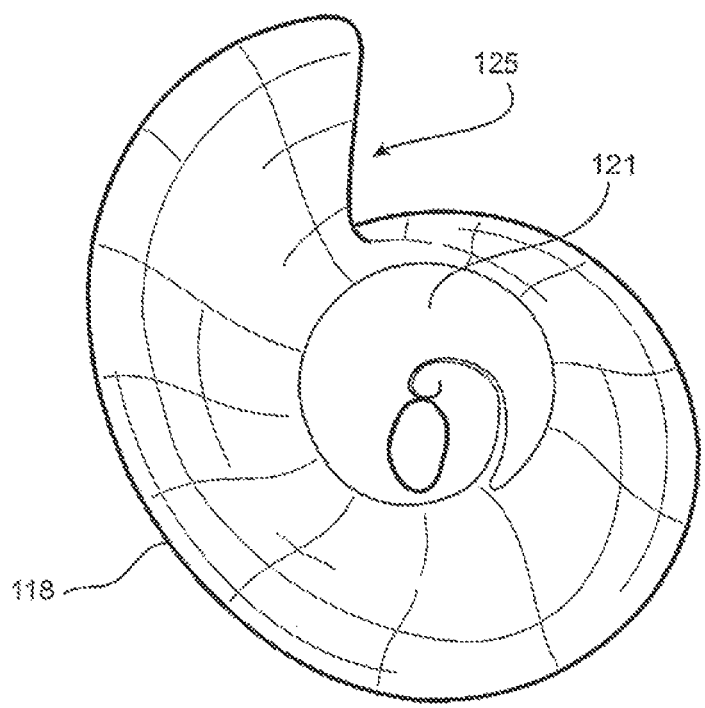
FIG. 9 is an end view of a duct according to the fourth embodiment.

A third embodiment shown in FIG. 7 depicts a duct (51) providing a twisting pathway (52) for fluids conforming to the Golden Section or Ratio. As fluid (53) flows through the inside or outside of the duct it is urged to conform to natural flow spiral characteristics, which minimize extraneous turbulence. Additionally, the diagram shows the fluid's spiralling flow path on the fluid as it flows.

An example of a duct constructed in accordance with the third embodiment is a cardiovascular stent. Conventionally, stents have been cylindrical in shape. While intended to be permanently placed within the patient, it has been found in many cases, that fatty deposits are formed within the stent over a period of time, requiring their replacement. It is believed that this build up is caused as a result of the turbulence in the stent. A stent constructed in accordance with the third embodiment will avoid this turbulent flow and thereby prevent the formation of fatty deposits in the stent.

Figure 10:
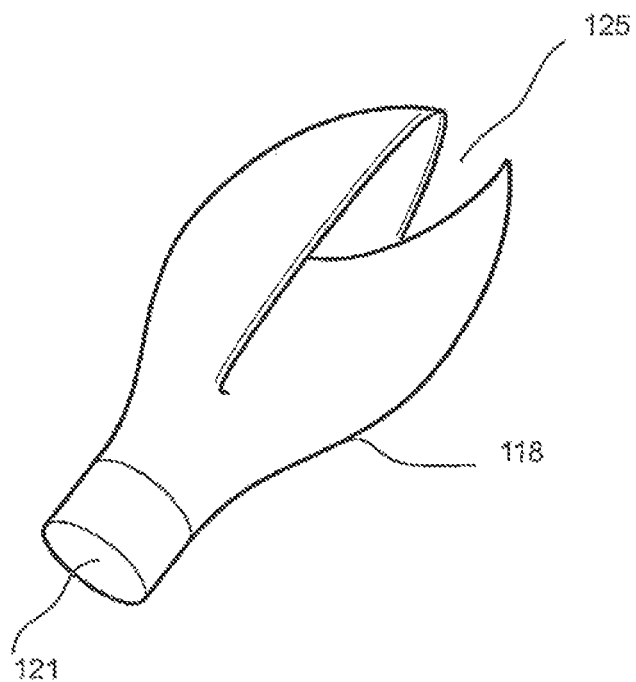
FIG. 10 is an isometric view of a duct according to a fifth embodiment.
Figure 11:
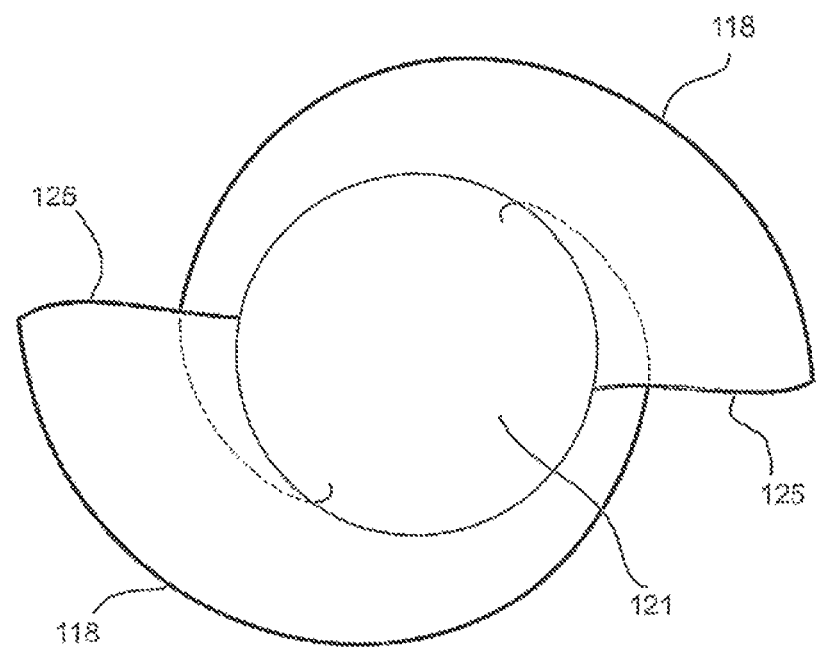
FIG. 11 is an end view of a duct according to the fifth embodiment.

The fourth embodiments as shown at FIGS. 8, 9, 10 and 11 each comprises a fluid flow controller 118 which generally takes the form of a shell of the phylum Mollusca, class Gastropoda, genus *Volutidae* as shown at FIGS. 8 and 9 and 10 and 11 where the inner end of the shell is cut away as shown to provide an entry (121) into the interior of the shell. The mouth of the shell serves as the outlet (125) for the controller 118. FIGS. 10 and 11 show twin ducts. The controllers according to the fourth embodiments are placed along the fluid flow path to induce a fluid flow that conforms with Nature.

A further embodiment relates to a muffler or sound attenuator for a sound source such as an internal combustion engine. It also serves the function of a flame duct or tube to maximise fuel/air combustion and exhaust gas extraction from an internal combustion engine and/or the optimum extraction of energy via adiabatic expansion. The invention also has application to mufflers, flame tubes and exhaust systems.

A typical exhaust system will have a length of exhaust pipe extending from the engine for sufficient distance to provide an effective flame tube, a contained area in which gas turbulence is minimised and a harmonic is created. This then enters a muffler which is usually a box or chamber with an inlet pipe and outlet pipe. There are baffles, or obstructions within the box which slow down the exhaust gases passing through the box. The box itself, being larger than the inlet pipe allows the exhaust gas to expand, thereby slowing the gas. These reductions in gas speed result in a reduction in noise.

Muffler systems of this type can suffer from operational difficulties and inefficiencies i.e. the baffling and slowing of exhaust gases in this way causes turbulence and back pressure on the gas and therefore at exhaust of the engine, resulting in reduced performance and efficiency. For example, to maximise power output from an engine, racing cars and bikes have no mufflers on their exhaust systems but, instead use tuned flame tube ducts which act as extractors of exhaust gases, thereby reducing turbulence and maximising engine power output as a result. They are, of course, very noisy.

Inefficiencies of gas movement through turbulence may be caused by a number of different reasons but is exacerbated by sudden or abrupt changes in direction or velocity of the gases passing through the muffler.

To this end, the flame tube/exhaust pipe may be applications of the flow controller of the second, third or fourth embodiments to thereby improve the efficiency of the system.

The muffler according to the present invention aims to overcome these problems by providing a muffler which acts as an expansion chamber configuration to reduce the severity of changes in speed or velocity of the gases passing through it, thereby reducing the noise in the system. The embodiment also seeks to take advantage of natural fluid movement tendency which has been observed in Nature to generally form vortices which have a logarithmic spiral. These spiral expansion-contraction ratios, as used in the invention, also offer the path of maximum non turbulent adiabatic expansion for gases and therefore provides for greatest efficiency in steam expansion ducts/chambers.

In one form of the embodiment there is provided a rotational-formed expansion chamber which acts as a chamber or expansion tube. The duct is shaped and expanded to a logarithmic curve configuration. Preferably the logarithmic curve is arranged so that the entry of gas is at the fine end and the exit is at the coarse or wider end of the chamber.

Where the term logarithmic curve, or logarithmic progression has been used it is to be understood that any form of curve following a logarithmic progression is included within this definition, including so-called exponential configurations. Any curve which approximates an equiangular logarithmic curve is also included within the term "logarithmic curve" used in this specification.

Although many forms of logarithmic curve configuration for exhaust ducts may be used and may achieve desired effects, i.e. the reduction of cavitation and the more efficient exhausting and silencing of gases and optimised adiabatic expansion, it is felt that the preferred logarithmic progression is that curve referred to as "the Golden Ratio" in which the logarithmic curve fits within a series of conjoint rectangles, each having their sides in the approximate proportion of 1:0.618.

The embodiment stems from a desire to decelerate the gases in an exhaust system in a manner in which is harmonious with the natural forms of movement of gases. The embodiment establishes largely singular, vortical flow with minimal counterproductive turbulence which is extraneous to main flow. It is also designed to optimise inherent flame tube/duct characteristics for the maximum combustion of gases.

It has been observed that in nature that natural vortices of whirlpools have a shape which generally follows a logarithmic progression. The embodiment aims to move and decelerate the gases within an exhaust system duct by the use of vanes or expansion chambers formed to a logarithmic curve so that the gas is caused to decelerate or gradually at first followed by a progressively increasing change of speed in a continual direction change approximating a Golden Ratio logarithmic progression. By acting on the working medium in this manner, the cause of sudden decelerations or radical changes of direction is reduced and the potential for turbulence and poor performance of the muffler/flame tube duct is also reduced.

Mufflers using a rotationally formed logarithmically expanding duct according to the embodiment may be used in any suitable application for the expansion and/or muffling of gases, and even for the extraction of air and other gases, but typically finds application in internal combustion engine exhaust systems. In this application the gas can be induced through the entry to the duct system, decelerated smoothly using the logarithmic curved vanes and/or chambers, in harmony with the naturally occurring responses of the gas, and ejected at low velocity to cause slowing and noise reduction of gases.

To this end a muffler may be provided in a large number of different configurations which are typified by the examples shown in the accompanying drawings.

Figure 12:
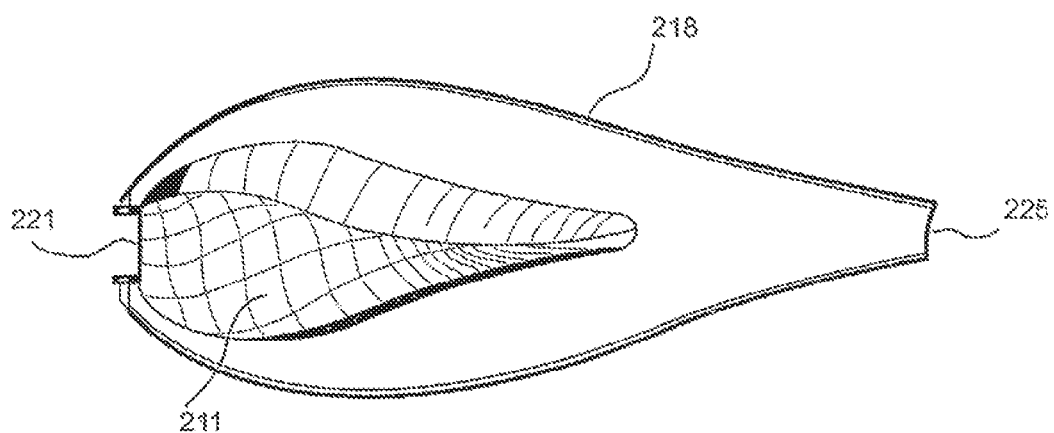
FIG. 12 is a diagrammatic side elevation (partially sectionalised) of an expansion chamber according to a sixth embodiment.

In the form of the embodiment shown in FIG. 12 there is shown a muffler (218)/expansion chamber (211) having an entry section (221) and an exit section (225) in the form of a converging or diverging duct respectively. The muffler is shaped to follow a logarithmic curve having a fine pitch in the area (221) adjacent the inlet and the relatively coarse pitch in the area adjacent the outlet (225). Gases forced into the inlet (221) are caused to slowly decelerate and rotate in a vortex movement, following a natural movement for gases.

Figure 13:
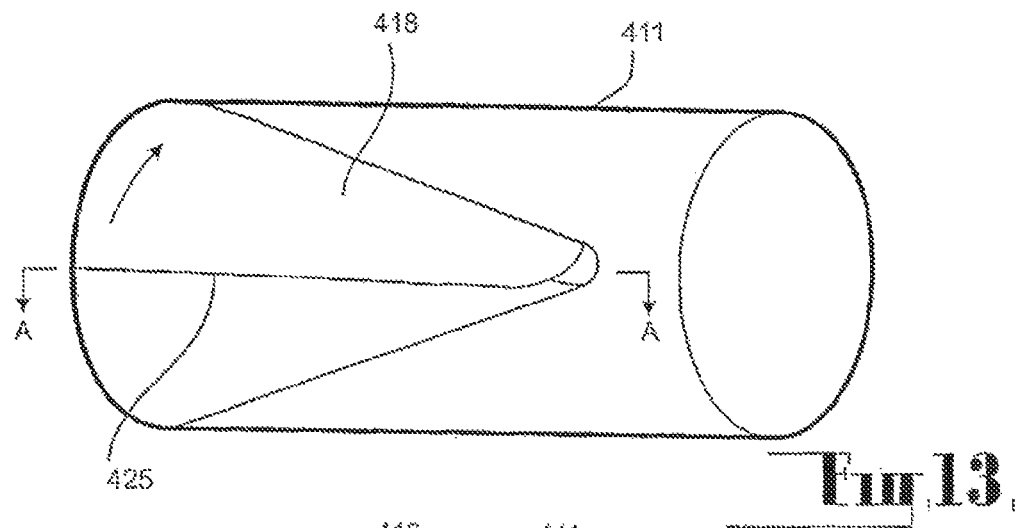
FIG. 13 is a cross-sectional view of the seventh embodiment.
Figure 14:
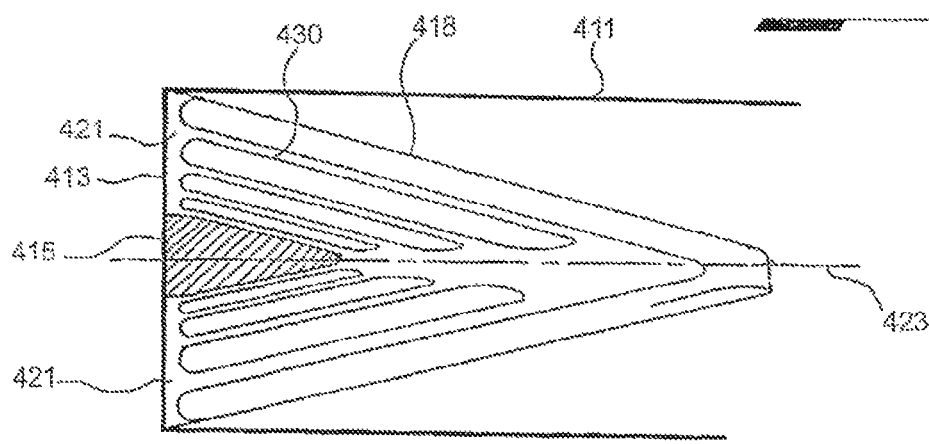
FIG. 14 is a diagrammatic isometric view of an expansion chamber according to a seventh embodiment.
Figure 15:
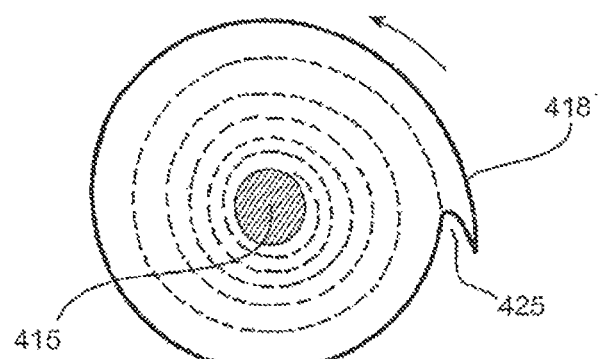
FIG. 15 is an end view of the seventh embodiment as shown in FIG. 14.

In the configuration of the form of the embodiment shown in FIGS. 13, 14, and 15, the expansion chamber may be located within a shroud (411). The chamber has a spiral wall orientated about an axis (423) and having an edge (425) from which the conical wall spirals inwardly in a manner following a logarithmic progression. The cross section of the cavity between adjacent walls increases outwardly in a logarithmic progression causing deceleration of the fluid within the cavity. Rotation of the gas in the chamber is in a clockwise sense (with regard to FIG. 8), inducted through entry (415) and forced through the outwardly tapering spiral canals within the impeller until it is thrust out through the exit (425).

The spiral tube forming the expansion chamber (418) preferably has a relatively large cross-section at the outlet (425) and a relatively small cross-section at the inlet (423), from which gas is inducted at high velocity and caused to be ejected from outlet (425) resulting in expanded, slowed noise, gas.

The configuration of the form of the embodiment of the chamber can be seen more clearly in FIG. 15 which is a typical view from the top of such a chamber from which it can be seen that the shape incorporates a logarithmic curve in its spiral configuration.

This logarithmic curve or spiral in the approximate ratio of 1:0.618 applied to chambers, vanes or ducts shaped according to this curve are able to operate in a harmonious manner with the natural movement of gas allowing these fluids to be decelerated through a chamber or motor in a manner which is considerably more harmonious, and therefore efficient than that achieved in conventional mufflers, expansion chambers and flame tubes.

It is a common characteristic of each of the embodiments described above that they can be used as a duct which can induce fluid flow in a non-turbulent manner between an inlet and an outlet or alternatively which permits the passage of fluid between the inlet and outlet in a substantially non-turbulent, more efficient manner than has been possible with conventional ducts of equivalent capacity.

In addition it is a characteristic of the invention that the duct of the invention and each of the embodiments can be used with gaseous, liquid and slurry forms of fluid medium.

It is a further characteristic of the invention that the flow of fluid over the surface of the duct results in significantly less friction and impact forces being imposed upon the surface and the duct. As a result of this and the reduced turbulence created by the duct there is less heat and noise generated as a result of the action of the duct and thus imparted into the fluid.

It is a further characteristic of the invention that the induced vortical flow of the fluid reduces sedimentation of materials in suspension on the walls of the duct.

It is a further characteristic of the invention that the reduced cavitation of liquids result in reduced oxygenation and therefore reduced oxidization of the liquids or duct construction materials.

It is a further characteristic of the invention that fluids may pass through it in reverse flow to produce opposite effects.

Additionally, in the embodiments the inlet provides the minimum clearance for the fluid entering the duct and as a result any materials which are able pass into the inlet will be able to pass through the duct which reduces the possibility of the duct becoming clogged.

The duct of the invention has application to use in, among others: plumbing systems, refrigeration, circulatory piping or ducting systems, hot gas or refrigerant gas expansion/contraction systems, afterburners, smoke stacks, flues, combustion chambers, air-conditioning ducts, dust precipitators, sound attenuators and mufflers, and can be used to advantage in any proposed application of such, at least because of the enhanced fluid flow, reduced friction, and reduced heat gain, reduced sedimentation, reduced oxidisation, and reduced noise.

It should be appreciated that the scope of the present invention need not be limited to the particular scope described above.

Throughout the specification, unless the context requires otherwise, the word "comprise" or variations such as "comprises" or "comprising", will be understood to imply the inclusion of a stated integer or group of integers but not the exclusion of any other integer or group of integers.

What is claimed is:

1. A duct comprising:
    an inlet for receiving the fluid;
    an outlet for expelling the fluid; and
    an intermediate fluid pathway between the inlet and the outlet, the intermediate fluid pathway excluding a substantially right angle bend and including a curvature between the inlet and the outlet, the curvature inducing vortical flow that reduces turbulence in the fluid flow as the fluid traverses the intermediate fluid pathway, and wherein the curvature substantially unfolds at a constant order of growth when measured at equiangular radii between the inlet and the outlet.

2. The duct of claim 1 wherein the curvature is configured to facilitate a change of direction in the flow of a fluid.

3. The duct of claim 1 wherein the curvature comprises a spiral twist between the inlet and the outlet.

4. The duct of claim 1 wherein the curvature comprises a helical twist between the inlet and the outlet.

5. The duct of claim 4 wherein the duct comprises a cardiovascular stent.

6. he duct of claim 1 wherein the curvature is substantially in the form of a shell configuration from the phylum Mollusca, class Gastropoda, genus *Volutidae*.

7. The duct of claim 6 wherein the duct comprises a fluid flow controller for reducing turbulence in fluid flow.

8. A duct comprising:
    an inlet for receiving the fluid;
    an outlet for expelling the fluid; and
    an intermediate fluid pathway between the inlet and the outlet, the intermediate fluid pathway excluding a substantially right angle bend and including a curvature between the inlet and the outlet, the curvature inducing vortical flow that reduces turbulence in the fluid flow as the fluid traverses the intermediate fluid pathway, and wherein the curvature is substantially in the form of a shell configuration from the phylum Mollusca, class Gastropoda, genus *Volutidae*.

9. The duct of claim 8 wherein the duct comprises a fluid flow controller for reducing turbulence in fluid flow.

* * * * *